United States Patent [19]

Layzell et al.

[11] Patent Number: 5,302,268

[45] Date of Patent: Apr. 12, 1994

[54] ELECTROLYTIC APPARATUS FOR GENERATING SELECTED CONCENTRATIONS OF GAS IN A FLOWING GAS STREAM

[75] Inventors: David B. Layzell; Stephen Hunt; Adrian N. Dowling, all of Kingston, Canada

[73] Assignee: Queen's University, Kingston, Canada

[21] Appl. No.: 27,511

[22] Filed: Mar. 4, 1993

[51] Int. Cl.⁵ .......................... C25B 9/00; C25B 15/08
[52] U.S. Cl. .................................. 204/228; 204/277; 204/278
[58] Field of Search ................ 204/277–278, 204/228, 229, 230, 250

[56] References Cited

U.S. PATENT DOCUMENTS

| | | | |
|---|---|---|---|
| 1,034,646 | 8/1912 | Rabenalt | 204/278 X |
| 3,527,690 | 9/1970 | Bellay et al. | 204/277 X |
| 3,630,860 | 12/1971 | Fox | 204/277 X |
| 4,056,968 | 11/1977 | Winslow | 73/19 |
| 4,233,132 | 11/1980 | Carr et al. | 204/278 X |
| 4,293,399 | 10/1981 | Belanger et al. | 204/195 P |
| 4,298,572 | 11/1981 | Moffet et al. | 422/68 |
| 4,454,748 | 6/1984 | Terai et al. | 73/19 |
| 4,520,654 | 6/1985 | Terhune | 73/24 |
| 4,605,626 | 8/1986 | Beck | 204/277 X |
| 4,781,811 | 11/1988 | Mankut et al. | 204/278 X |
| 4,977,766 | 2/1990 | Shindo et al. | 73/19 |

Primary Examiner—Donald R. Valentine
Attorney, Agent, or Firm—Richard J. Hicks

[57] ABSTRACT

An apparatus for electrolytically generating small volumes of a selected gas such as hydrogen for introduction into a flowing gas stream is described. The gas stream flows through an electrolytic cell wherein the selected gas is generated at an electrode and a portion of the gas stream is diverted through a needle valve and a non-conducting capillary with a small orifice to deliver gas to the electrodes so as to dislodge the selected gas bubbles forming thereon and carry them into the flowing gas stream. To maintain the level of electrolyte in the cell, the cell is connected by a narrow tube to a reservoir of electrolyte. The reservoir has a volume and surface area many times greater than that of the cell and the gas volume above the reservoir is maintained at the pressure and composition of the gas stream entering the electrolytic cell.

8 Claims, 4 Drawing Sheets

ELECTROLYTIC APPARATUS FOR GENERATING SELECTED CONCENTRATIONS OF GAS IN A FLOWING GAS STREAM

FIELD OF INVENTION

This invention relates to an apparatus for the electrolytic dissociation of an electrolyte to generate specific concentrations of $H_2$ or other gas in a flowing gas stream passing through the apparatus. More particularly the electrolytic device is for the generation and evolution of $H_2$ and is controlled so as to provide a stringently controlled concentration of $H_2$ in a gas stream which passes through, and across, the electrolyte. The apparatus is useful for providing known concentrations of $H_2$ for the calibration of $H_2$ sensing devices, and similarly other gases.

CROSS REFERENCE TO RELATED APPLICATION

This application is related to our co-pending application, titled GAS ANALYZER filed concurrently herewith.

BACKGROUND OF INVENTION AND PRIOR ART

Many devices have been designed for the electrolytic dissociation of water to produce $H_2$ and $O_2$ gases, for example U.S. Pat. No. 4,465,570 Y. Oda et al., 1984; U.S. Pat. No. 4,726,888 M. Mc Cambridge, 1988. Some devices are designed such that a gas stream, U.S. Pat. No. 4,124,463 A. H. Blue, 1978, or a stream of inert liquid, U.S. Pat. No. 4,226,683 V. A. Vaseen, 1980, passes across the electrodes to dislodge the gases evolved from the water. However, there is no electrolytic device currently available which is designed to produce known $H_2$ concentrations in a gas stream which purges the electrolytic cell. Such a device, if capable of producing low, stable concentrations of $H_2$, would be extremely useful for the calibration of analytical instruments which measure low concentrations of $H_2$ in a flowing gas stream. In order to produce stable $H_2$ standard gases by electrolysis, the $H_2$ evolved at the electrodes must be removed as it is formed, rather than accumulating in bubbles at the electrode surface. If bubbles are allowed to form, they produce irregularities in the $H_2$ content of the gas in the air space above the electrolyte. The $H_2$ generating device described in the present application minimizes bubble formation by reducing the surfaces on which bubbles may collect, and by passing a gas stream across the electrode surfaces during dissociation of water. In this way, $H_2$ is swept away from the electrodes as soon as it is formed, and the accumulation of $H_2$ in the air space above the electrolyte is determined only by the current supplied to the electrodes and the rate of gas flow through the air space.

Usual methods for calibrating instruments for the detection of low concentrations (of the order of a few parts per million) of gaseous $H_2$ generally involve the use of pressurized gas cylinders containing $H_2$ of known concentration, or the production of $H_2$ standard gas mixtures using pressurized gases attached to gas mixing pumps. Both of these methods require adequate space for the storage and use of pressurized gases, and are also expensive in the long term. The $H_2$ generating unit described herein requires little space and is inexpensive compared to accurate gas mixing devices or the cumulative cost of purchasing special $H_2$ standard gases. An example of an instrument which could be calibrated using the electrolysis unit described in this patent application is a nitrogenase activity analysis system (NAAS) which measures nitrogenase activity as the rate of $H_2$ evolution from $N_2$-fixing plant material. The NAAS is described in detail in copending patent application entitled An Apparatus for Measuring Low Concentrations of Gases in a Flowing Gas Stream, filed concurrently herewith and commonly assigned.

OBJECT OF THE INVENTION

It is one object of the invention to provide an apparatus for the electrolytic dissociation of water which generates and evolves $H_2$ gas of known concentration into a flowing gas stream.

It is another object of the invention to provide an apparatus which can be used for the calibration of instruments which measure low concentrations of gaseous $H_2$.

BRIEF STATEMENT OF INVENTION

Thus by one aspect of this invention there is provided an apparatus for generating a selected concentration of a selected gas flowing in a gas stream comprising:
(a) electrolyte cell means, adapted to contain a selected electrolyte, and having a gas inlet means and a gas outlet means with a gas flow path therebetween;
(b) reservoir means to supply said cell means with a supply of said electrolyte such that the level of electrolyte within the cell remains constant;
(c) electrode means in said cell means, between said gas inlet means and said gas outlet means, arranged for immersion in said electrolyte;
(d) means to supply a selected electrical current to said electrode means;
(e) means to supply a gas stream to said gas inlet means;
(f) means to introduce a portion of said gas stream into said electrolyte contained in said cell means and direct said portion towards said electrode means so as to dislodge gas bubbles forming thereon, when said electrical current is applied, and into said gas stream in said flow path;
(g) means to balance the gas pressure within the said cell means and above the said reservoir means by directing said portion of said gas stream through the gas phase above the reservoir before entering electrolyte in said cell means.

DETAILED DESCRIPTION OF PREFERRED EMBODIMENTS

Figure 1:
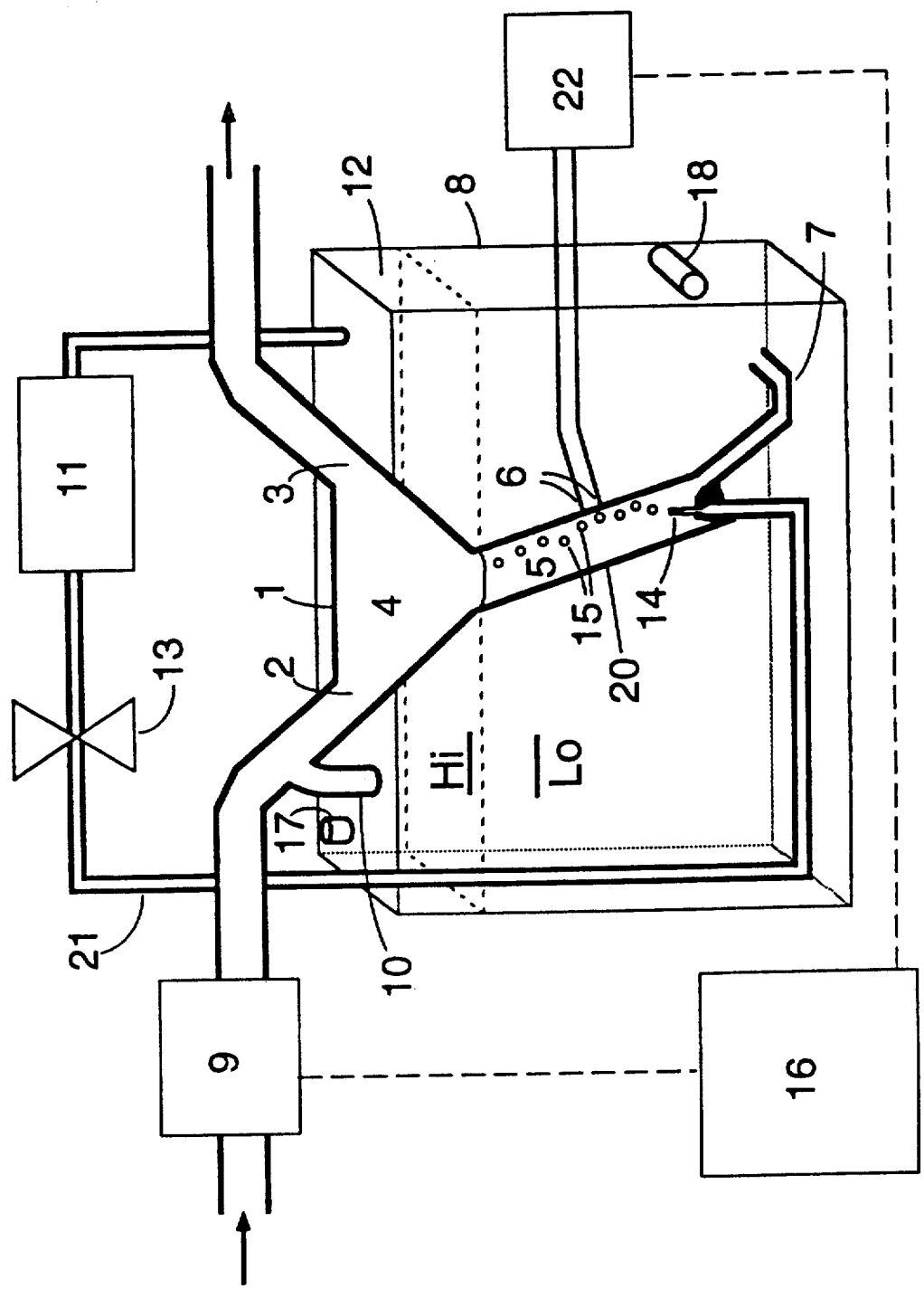
FIG. 1 is a block diagram of one embodiment of an electrolysis unit of the present invention.

A preferred embodiment of the H$_2$ generating system is illustrated in FIG. 1. The electrolytic cell (1) is constructed of a non-conducting material such as plastic or glass. The cell has a gas inlet port (2), a gas outlet port (3) and a lower chamber (20) containing an electrolyte (5) and a pair of electrodes (6). A gas space (4) is present above the electrolyte (5) and functions to separate the electrolyte from the gas stream thereby preventing the electrolyte from being swept out of the outlet port (3). In the embodiment of the apparatus illustrated, the cell (1) is Y-shaped, although other configurations may be used which allow the input gas to entirely flush the gas space (4) above the electrolyte before exiting the cell. The lower chamber of the electrolytic cell (20) has an input port comprising a capillary tube (14) made of non-conducting material, such as glass, with an orifice of approximately 0.5 mm diameter or less. The capillary projects into the electrolyte within the cell, and is connected to gas flow path (21).

A second tube (7) with a small orifice is provided in the bottom of the electrolytic cell (20) and is connected to reservoir (8) of electrolytic solution (5). The reservoir (8) is not entirely filled with electrolytic solution, but contains a gas space (12) above the solution. The level of electrolytic solution is maintained between high (Hi) and low (Lo) markings on the side of the reservoir by injection of solution into the reservoir through a port (17) into the reservoir (8) or by removal of solution through a drainage port (18). The drainage port is preferably positioned to allow it to also be used, if necessary, to insert a wire, etc. to clean the small orifice tubing (7) connecting the reservoir to the electrolytic cell. The volume of electrolyte in the reservoir, and the surface area of the electrolyte exposed to the gas space above the reservoir, are many times greater than the volume and exposed surface area of the electrolyte in the electrolytic cell. Gravitational flow of electrolyte from the reservoir to the electrolytic cell via tube (7) maintains the electrolyte in the cell at a constant level.

The flow rate of the gas entering the electrolysis unit is monitored by a flow meter (9) preferably, though not essentially, of the electronic type so that its voltage output can be recorded by a computer or analog recording means. After passage through the flow meter, the gas is divided into major and minor streams. The major stream passes into the gas inlet port (2) of the electrolysis unit, through the gas space (4) above the electrolyte in the cell (20) and out through the outlet port (3). The minor gas stream is diverted from the major gas stream by entering a tube (10) connected to the gas space (12) over the electrolytic solution in the reservoir (8). This minor gas stream becomes the gas flow path (21) mentioned previously. A pump (11) draws the gas through tube 10, through the gas space (12) and passes it through a needle valve (13) to the capillary tube (14) entering the electrolytic cell (20). The flow rate of the gas is regulated to approximately 20 ml/min. by control of the voltage supply to the pump and the resistance of the needle valve 13.

The gas stream (15) emerging from the capillary (14) is directed towards the electrodes (6) so that the gas bubbles generated from the surfaces thereof are dislodged as soon as they are formed. The unit may be angled to optimize the flushing of the electrodes with the gas stream (15) issuing from the capillary. It should be noted that the presence of a continuous gas phase between the major gas passing through the electrolytic cell, the gas space (12) above the electrolyte in the reservoir (8) and the gas stream (15) issuing into the electrolyte via the capillary (14), equalizes gas pressures within the apparatus and prevents pressure-induced changes in the level of electrolyte within the electrolytic cell which may otherwise occur.

The electrodes (6) are made of a non-corroding, conductive material, such as platinum wire, and are ground at their tips until they are flush with the wall of the cell. Although this is not essential for electrode function, it helps to minimize surfaces where gas evolved at the electrodes can collect and form discrete bubbles. The electrodes are positioned relative to each other so that the minor gas stream (15) provided to the cell by tube (14) sweeps both their surfaces continuously. In the embodiment shown in FIG. 1, each electrode tip has a surface area of 0.5–2.0 mm$^2$ and the anode and cathode are positioned 2 mm apart and equidistant from the base of the cell and from the surface of the electrolyte. This configuration produces stable rates of H$_2$ production when the electrodes are immersed in 0.8 cm$^3$ of electrolyte and are swept with a gas stream issuing from the capillary at approximately 20 ml/min. Larger, or smaller, electrolysis units of the same type may need different configurations and flow rates to produce stable rates of H$_2$ production. It will be appreciated that in the electrolytic dissociation of water, a stoichiometric amount of O$_2$ is also generated, i.e. half the volume of H$_2$. At the levels of H$_2$ production generated by the apparatus, in the ppm range, this amount of O$_2$ is not generally measurable against the background of O$_2$ in the atmosphere.

Figure 3:
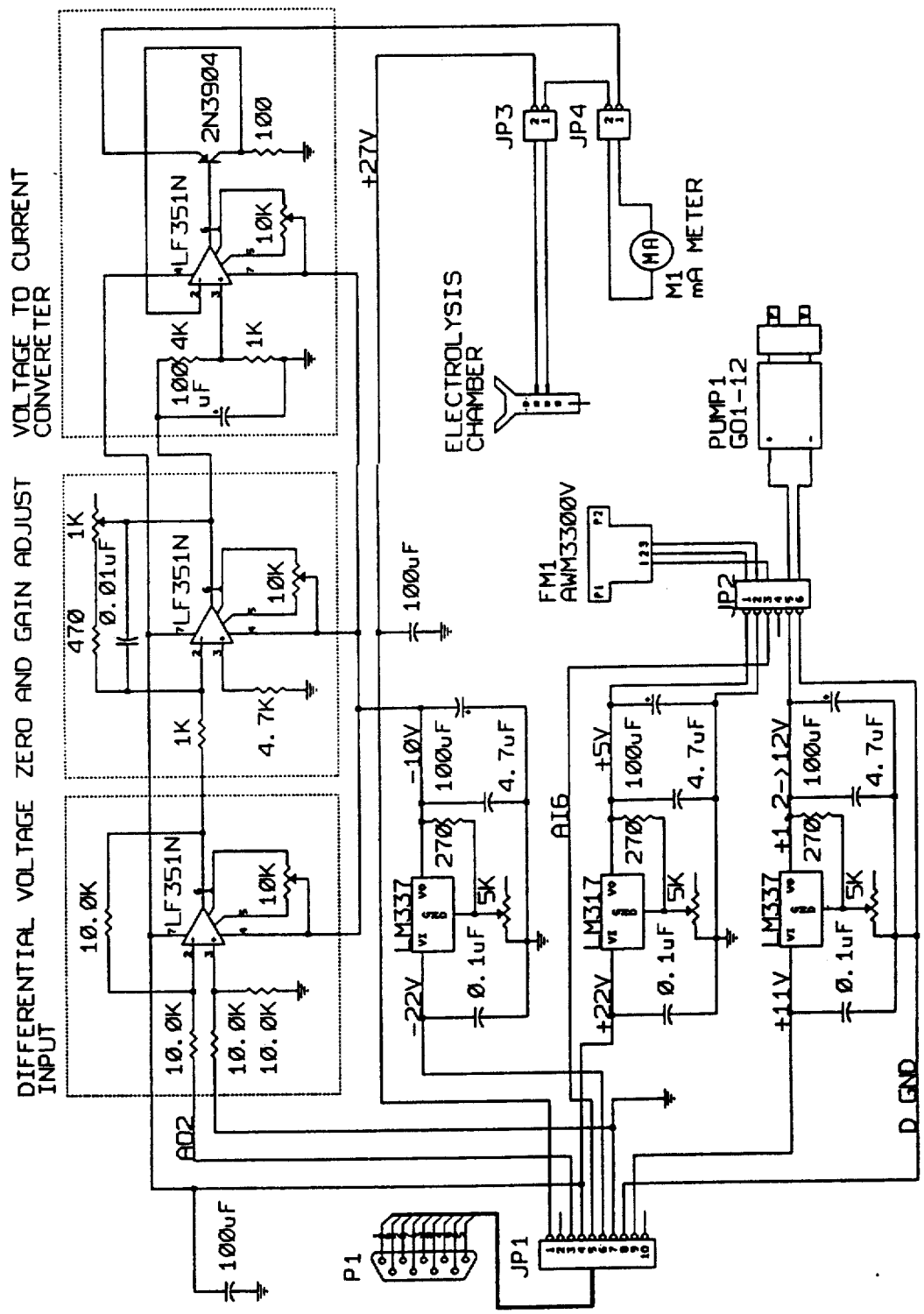
FIG. 3 is a schematic diagram of the electronic control system of the electrolysis unit of FIG. 1.

The electrolyte in which the electrodes are immersed is preferably an acid such as 0.1N hydrochloric acid, although other aqueous solutions of acids of salts can be used to generate H$_2$ from dissociation of water. It will be appreciated that the greater the concentration of electrolyte used in the cell, the lower the voltage which is needed to generate the current required for the electrolysis of water. It should be noted, however, that the data presented herein (FIG. 3 and FIG. 4) were obtained using an electrolyte consisting of 0.1N hydrochloric acid.

Figure 4:
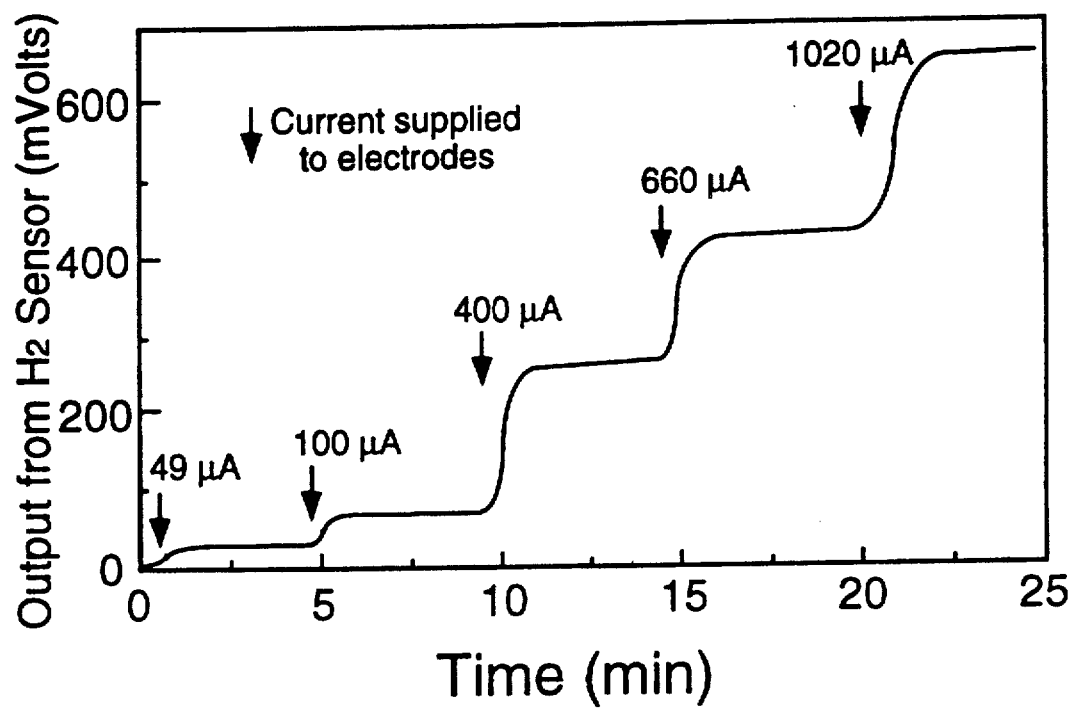
FIG. 4 is a graph showing a typical time course of $H_2$ generation from the electrolysis unit as current output to the electrodes is increased in a stepwise fashion.

During initial operation of the electrolysis unit, the flow rate of gas passing through the capillary (14), and the angle of the electrolytic cell, are adjusted until a constant rate of H$_2$ evolution is measured from the unit. The amount of H$_2$ generated by the unit is dependent on the voltage supplied to a control circuit (22) which, in turn, provides a highly regulated current supply across the electrodes (6). Initially, the relationship between voltage, current and H$_2$ production is determined empirically by comparing H$_2$ production from the unit against known H$_2$ standards. However, this relationship is stable and, once it is determined, H$_2$ can be produced at a desired rate by supplying an appropriate voltage to the electrode via the control circuit (22) computer under control, from a conventional power source (not shown). In the embodiment shown in FIG. 1 a current of 1 to 3.3 mAmps produces 1 to 50 ppm H$_2$ in the effluent gas stream when the total flow rate of gas entering the electrolysis unit (measured by the flow meter) is 500 ml/min. The relationship between H$_2$ production and current is linear (FIG. 2), so that extremely fine control over H$_2$ concentration can be obtained by similarly fine control over current supply. This is achieved by the control circuit (FIG. 3) which is equipped with operational amplifiers configured to provide zero and gain control and a highly stable voltage signal as the setpoint on a current control circuit. The time course of $H_2$ production with increases in voltage and current supply is shown in FIG. 4. Typically, $H_2$ production reaches a new steady state within 4 min of a change in voltage supply to the control circuit. However, this time will vary as it is dependent on the physical size of the electrolysis unit and on the flow rate of gas through it. Minor fluctuations in $H_2$ output from the unit that may occur at lower flow rates or at high rates of $H_2$ production, may be dampened by adding a mixing volume to the gas outlet (3).

Figure 2:
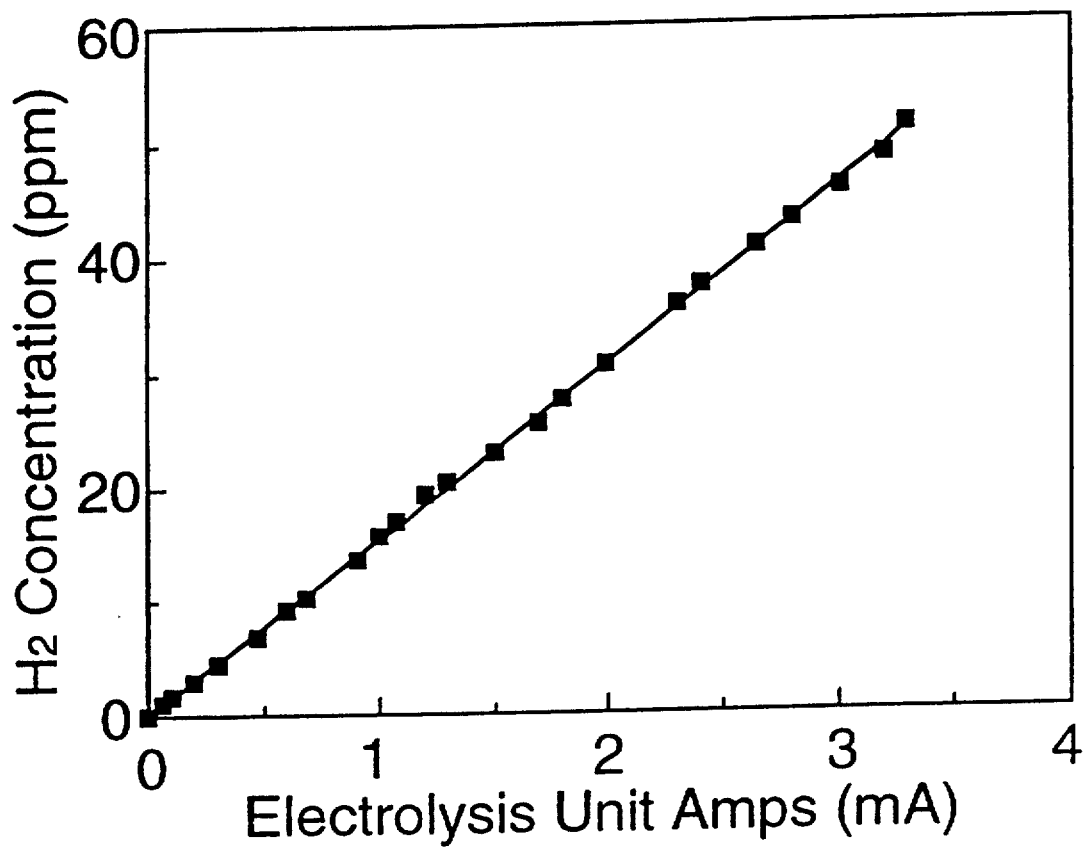
FIG. 2 is a graph showing the relationship between $H_2$ concentration in the gas stream emerging from the electrolysis unit of FIG. 1 and current supplied to the electrodes.

It will be appreciated from the data presented in FIG. 2 and FIG. 4 that the $H_2$ generating system described herein has the ability to generate a range of low, stable concentrations of $H_2$ in a flowing gas stream. If the flow rate of gas through the unit is known, the relationship between current supply to the electrodes and $H_2$ generation rate can be used to produce $H_2$ concentrations over a defined range. The electrolysis unit is, therefore, a very valuable device for calibrating sensors which are designed for the measurement of low concentrations of $H_2$ gas.

As a safety feature, the current supply to the electrolysis chamber from the control circuit (22) can be controlled by the computer (16) and only activated if the flow rate measured by the flow meter (9) is greater than some critical value. This would ensure that the $H_2$ concentration in the electrolysis chamber is maintained below a level where it is potentially explosive.

While this invention has been described with particular reference to $H_2$ generation, it will be appreciated by those skilled in the art that by selecting an alternative electrolyte, other gases such as chlorine, fluorine, and oxygen can equally well be generated in the appropriate quantities for use in calibrating their respective sensors and the like.

We claim:

1. An apparatus for generating a selected concentration of a selected gas flowing in a gas stream, comprising:
   (a) electrolyte cell means, adapted to contain a selected electrolyte, and having a gas inlet means and a gas outlet means with a gas flow path therebetween;
   (b) electrode means in said cell means, between said gas inlet means and said gas outlet means, arranged for immersion in said electrolyte;
   (c) means to supply a selected electrical current to said electrode means;
   (d) means to supply a gas stream to said gas inlet means;
   (e) means to introduce a portion of said gas stream into said cell means and direct said portion towards said electrode means so as to dislodge gas bubbles forming thereon, when said electrical current is applied, and into said stream in said flow path.

2. An apparatus as claimed in claim 1 wherein said cell means comprises a Y-shaped vessel containing said gas inlet means and said gas outlet means in adjacent upper arms thereof and said lower arm is adapted to contain electrolyte.

3. An apparatus as claimed in claim 2 wherein said electrode means are mounted flush in said lower arm.

4. An apparatus as claimed in claim 3 wherein said means to introduce a portion of said gas stream into said electrolyte comprises electrically nonconducting capillary means.

5. An apparatus as claimed in claim 4 including means to control gas flow through said capillary means.

6. An apparatus as claimed in claim 5 including electronic means to control said means to supply said gas stream, and said means to supply said current.

7. An apparatus as claimed in claim 1 including reservoir means to supply said cell means with electrolyte so as to provide a constant level of electrolyte in said cell means.

8. An apparatus as claimed in claim 7 including means to balance gas pressure within said cell means and said reservoir means.

* * * * *